US006679437B2

(12) United States Patent
Truelove

(10) Patent No.: US 6,679,437 B2
(45) Date of Patent: Jan. 20, 2004

(54) PRESSURIZED SPRAYER

(76) Inventor: Sean Truelove, 2011 E. Catclaw Ct., Gilbert, AZ (US) 85296

( * ) Notice: Subject to any disclaimer, the term of this patent is extended or adjusted under 35 U.S.C. 154(b) by 192 days.

(21) Appl. No.: 09/932,199

(22) Filed: Aug. 17, 2001

(65) Prior Publication Data

US 2003/0034404 A1 Feb. 20, 2003

(51) Int. Cl.[7] .................... A62C 15/00; A62C 13/62; A62C 15/02; A61M 11/02

(52) U.S. Cl. .................... 239/154; 239/303; 239/310; 239/366

(58) Field of Search .................... 239/154, 302, 239/303, 304, 307, 308, 310, 311, 345, 338, 366, 368, 369, 373, 433, 434; 222/129.4, 145.5, 145.1, 145.6, 94

(56) References Cited

U.S. PATENT DOCUMENTS

| | | | | | |
|---|---|---|---|---|---|
| 4,272,019 | A | * | 6/1981 | Halaby, Jr. | 239/8 |
| 5,816,446 | A | * | 10/1998 | Steindorf et al. | 222/1 |
| 6,021,921 | A | * | 2/2000 | Lan et al. | 222/61 |

* cited by examiner

*Primary Examiner*—Davis Hwu
(74) *Attorney, Agent, or Firm*—Schmeiser, Olsen & Watts LLP

(57) ABSTRACT

A sprayer that includes two pressurized tanks physically and fluidly coupled to each other is disclosed. One tank is inverted with respect to the other so that the top of one tank is adjacent to the bottom of the other tank, and vice versa. One tank contains a propellant such as carbon dioxide and the other contains a tear agent or other chemical irritant. The invention includes a shut-off valve adapted to regulate the flow of the chemical, and a dispensing head for accurate, controllable delivery.

8 Claims, 2 Drawing Sheets

PRESSURIZED SPRAYER

BACKGROUND OF THE INVENTION

1. Technical Field

This invention generally relates to a sprayer for dispensing substances, and more specifically relates to a pressurized sprayer for dispensing substances adapted to alter or affect behavior.

2. Background Art

Pressurized sprayers adapted to deliver a substance to a target area have been used for many years, and in many contexts. One context where pressurized sprayers have become increasingly common is police work, including for self-defense and for crowd or riot control. There are a number of sprayers suitable for these uses that deliver behavior-altering or other chemicals by using the controlled release of pressure.

For reasons relating to both liability and, to an extent, society's attitude toward the humane treatment of criminals and suspected criminals, less-lethal and non-lethal methods of subduing an adversary are gaining popularity among police forces and other law-enforcement personnel. These methods allow a policeman to, for example, temporarily alter or control the behavior of an adversary, perhaps by inflicting temporary pain, without causing any permanent injury or damage. Substances such as pepper spray and tear gas fall into the general category of non-lethal enforcement tools. Pepper spray, tear gas, and other inflammatory or tear agents may be effectively delivered using pressurized sprayers.

Existing spray devices, however, share certain shortcomings that inhibit desired performance. The most significant shortcomings relate to portability, ease of use, and discharge angle. Many of the current devices are too heavy, bulky, or awkward to be effectively carried by a single person, especially while performing strenuous or dangerous activities like a foot chase or a struggle with a violent assailant. The design of many of the existing devices is such that they may be discharged only when held at a very specific angle, limiting their effectiveness. Others of the devices must be refilled or recharged using a time-consuming process in which the chemical may only drip slowly into its container under carefully controlled conditions of temperature and pressure. Still others, while portable, lack the capacity required for prolonged or heavy use.

SUMMARY OF THE INVENTION

Therefore, there exists a need for a portable sprayer that is easy to use and maintain, has sufficient capacity for prolonged use, and delivers an accurate, dependable chemical spray that is effective in behavior control or alteration. The present invention fills that need by providing a sprayer that includes two pressurized tanks physically and fluidly coupled to each other. One tank is inverted with respect to the other so that the top of one tank is adjacent to the bottom of the other tank, and vice versa. One tank contains a propellant such as carbon dioxide and the other contains a tear agent or other chemical irritant. The invention includes a shut-off valve adapted to regulate the flow of the chemical, and a dispensing head for accurate, controllable delivery.

BRIEF DESCRIPTION OF THE DRAWINGS

The foregoing and other features and advantages of the invention will be apparent from the following more particular description of specific embodiments of the invention, as illustrated in the accompanying drawings, wherein.

DETAILED DESCRIPTION OF EMBODIMENTS OF THE INVENTION

Figure 1:
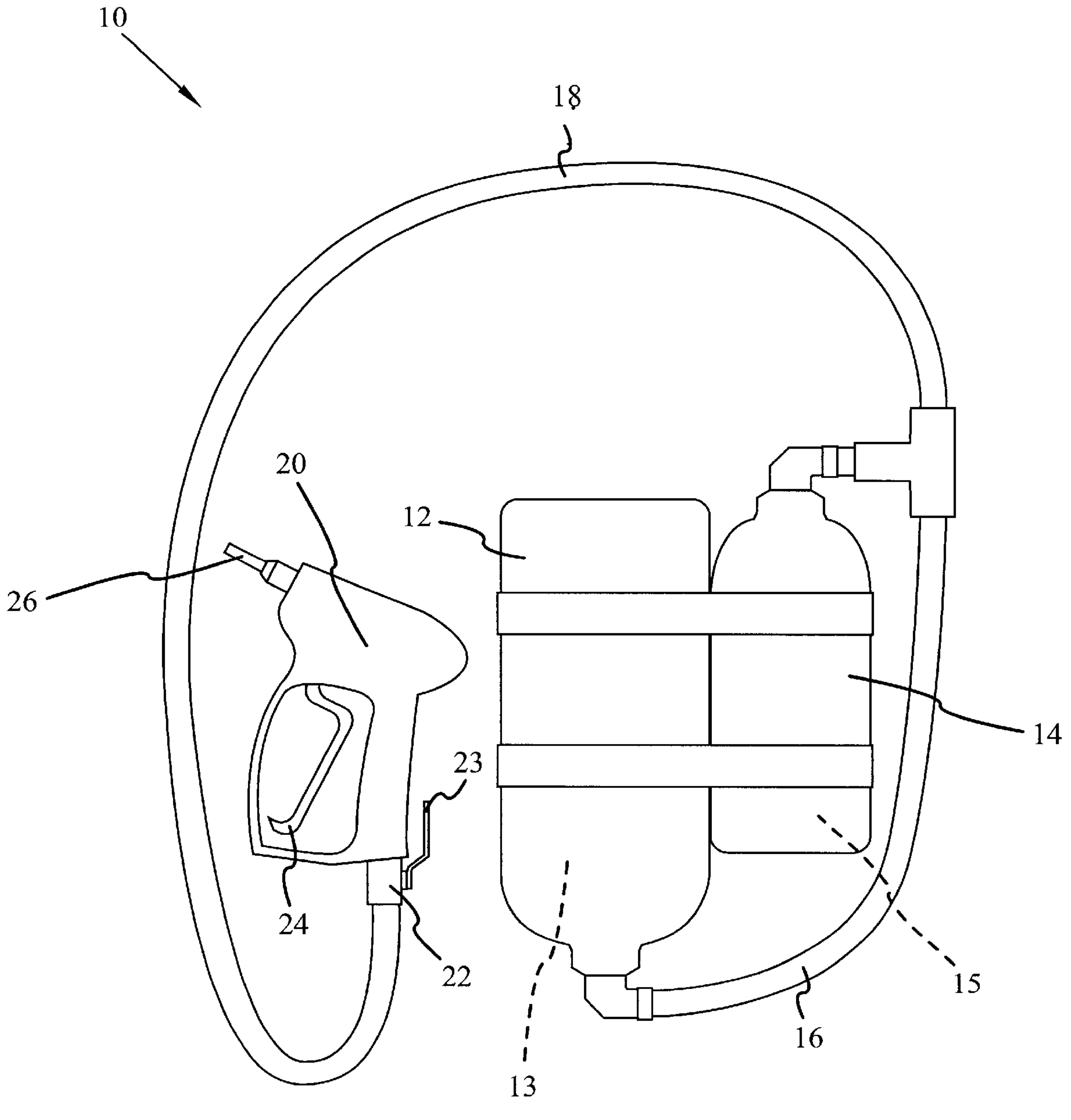
FIG. 1 is a view of a pressurized sprayer configured according to an embodiment of the present invention.

Referring now to the figures, and in particular to FIG. 1, a pressurized sprayer 10 includes a first pressurized tank 12 and a second pressurized tank 14. Pressurized tanks 12 and 14 may be inverted with respect to each other, for reasons relating to the flow of substances contained within pressurized sprayer 10, as will be explained in more detail below. A feed line 16 fluidly couples first pressurized tank 12 to second pressurized tank 14. A discharge line 18 fluidly couples pressurized tanks 12 and 14 to a dispensing head 20. A shut-off valve 22 is located between dispensing head 20 and pressurized tanks 12 and 14. Dispensing head 20 includes a trigger 24 and a nozzle 26.

First pressurized tank 12 is adapted to contain a first substance 13, not visible in the figure, and second pressurized tank 14 is adapted to contain a second substance 15, also not visible. First substance 13 may act as a propellant and second substance 15 may be a chemical irritant, although either one of pressurized tanks 12 and 14 may contain either the propellant or the chemical irritant. In one embodiment of the invention the propellant may be carbon dioxide ($CO_2$), although other propellants, for example nitrous oxide ($N_2O$) or liquified petroleum gas (LPG), are also possible. The chemical irritant may be, or may contain, tear gas, mace, oleoresin capsicum (the active ingredient in pepper spray), or any other physically irritating or behavior modifying substance suitable for delivery by a pressurized sprayer. As will be readily apparent to one of ordinary skill in the art, these may include all sorts of inflammatory agents, tear agents, and all other such chemicals or substances.

In one embodiment of the invention, first and second pressurized tanks 12 and 14 may be high pressure tanks. "High pressure" as used herein means a pressure equal to or exceeding 1500 psi. In one embodiment pressurized tanks 12 and 14 have a pressure equal or substantially equal to 2000 psi. It will be readily apparent to one of ordinary skill in the art that as pressurized sprayer 10 is used, and pressurized tanks 12 and 14 are emptied, the pressure inside pressurized tanks 12 and 14 will decrease. Thus, the term "high pressure tank" as used herein refers to a tank that, when initially placed under pressure and before any pressure is released, is placed under high pressure, as defined above. In one embodiment, the pressure in first pressurized tank 12 is greater than the pressure in second pressurized tank 14. This may be true whether or not first and second pressurized tanks 12 and 14 are high pressure tanks.

Dispensing head 20 may be any mechanism that delivers second substance 15 to a desired location. This delivery could take any of several forms, i.e. a cloud, a mist, a fog, a stream, a spray, or any other form that facilitates the delivery of substance 15 to a target, which may be an adversary that is to be subdued. In one embodiment of pressurized sprayer 10, dispensing head 20 may be adjustable to selectively deliver second substance 15 in any of two or more of the several forms. Nozzle 26 may act as a conduit through which first and second substances 13 and 15 flow before exiting pressurized sprayer 10. Trigger 24, when actuated, may create a pathway between nozzle 26 and pressurized tanks 12 and 14, thus causing the release of substances 13 and 15. When returned to its quiescent state, trigger 24 may close the pathway created by its actuation. Thus, trigger 24 may, in one particular embodiment of the invention, selectively permit and prevent the delivery of first and second substances 13 and 15.

Shut-off valve 22 may be adapted to regulate the flow of substances 13 and 15. Like trigger 24, shut-off valve 22 may, when in an open position, create a pathway between nozzle 26 and pressurized tanks 12 and 14, and, when in a closed position, close or block that pathway. Shut-off valve 22 may be any type of valve known in the art, including a ball valve, a check valve, a needle valve, or any other type of valve. In one embodiment, shut-off valve 22 may include a handle 23 that may be gripped and turned to move shut-off valve 22 from an open position to a closed position. Shut-off valve 22 may also be placed in a semi-open position, wherein the flow of substances 13 and 15 may be limited but not completely prevented.

In one embodiment of the invention, a second shut-off valve, not shown, may be included as part of pressurized sprayer 10. For example, the second shut-off valve may be placed in feed line 16 and be adapted to isolate first pressurized tank 12. This second shut-off valve may be similar in construction and function to shut-off valve 22.

Figure 2:
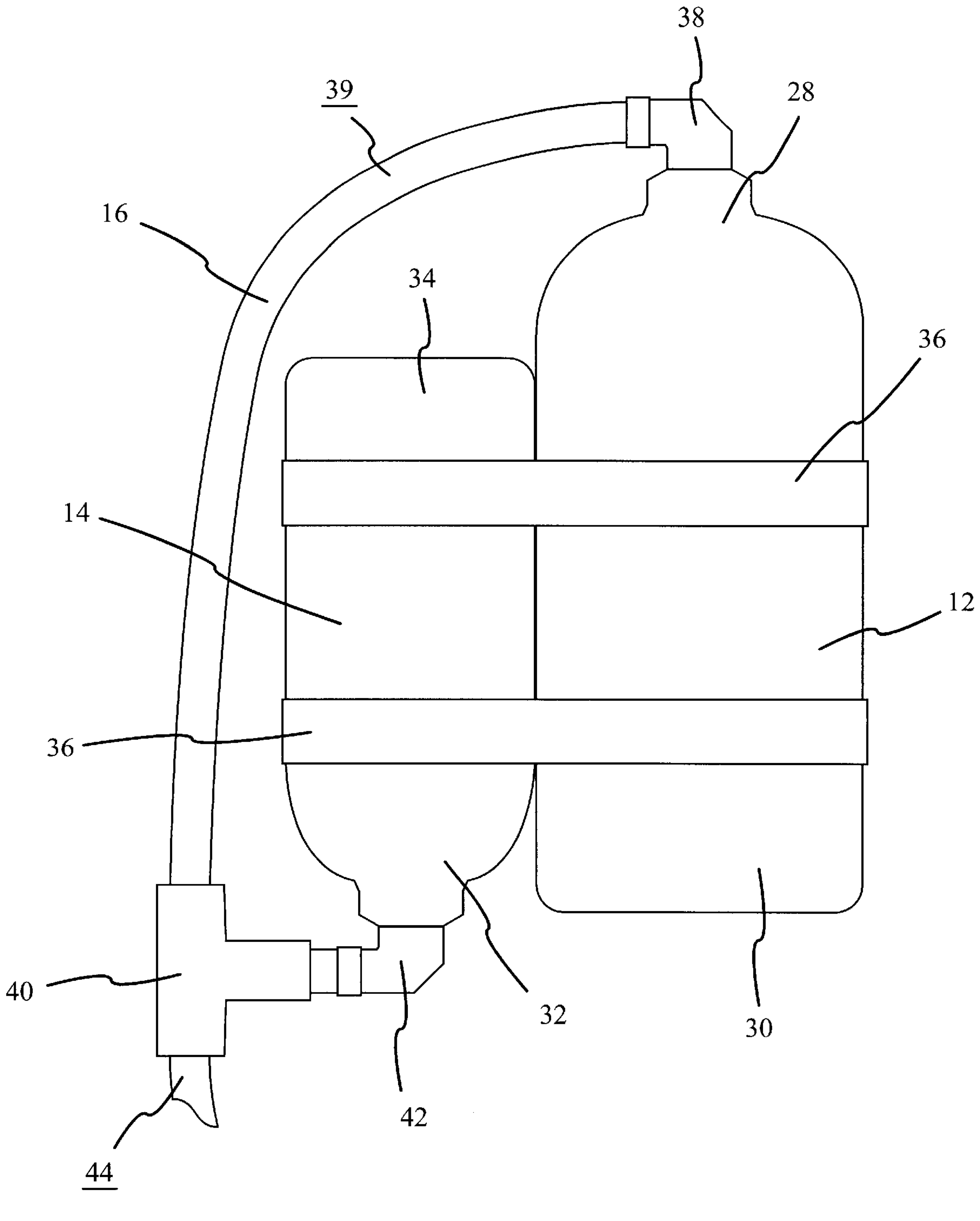
FIG. 2 is a detail view of a pressurized sprayer configured according to an embodiment of the present invention.

Referring now to FIG. 2, first pressurized tank 12 has an openable end 28 and a closed end 30. Second pressurized tank 14 also has an openable end 32 and a closed end 34. First pressurized tank 12 may be any size in relation to second pressurized tank 14, i.e., it may be larger than, smaller than, or the same size as second pressurized tank 14. The actual sizes, as well as the shapes, of pressurized tanks 12 and 14 may also vary. In one embodiment, pressurized tanks 12 and 14 are cylindrical, and are sized to be comfortably and easily portable by a single user, including being worn on the user's back like a backpack. Bands 36 hold first pressurized tank 12 adjacent to second pressurized tank 14, with openable end 28 adjacent to closed end 34, and with closed end 30 adjacent to openable end 32, i.e., with first pressurized tank 12 inverted with respect to second pressurized tank 14.

Feed line 16 fluidly couples first pressurized tank 12 to second pressurized tank 14, and includes a first elbow 38, a first length of tubing 39, a mixing tee 40, and a second elbow 42. Mixing tee 40 and a second length of tubing 44 make up discharge line 18.

Openable ends 28 and 32 may be the only portions of pressurized tanks 12 and 14, respectively, through which first and second substances 13 and 15 may enter and leave pressurized tanks 12 and 14. For example, second substance 15 may be poured through openable end 32 into second pressurized tank 14 in a conventional manner. Openable end 32 may be large enough that second pressurized tank 14 may be easily filled with second substance 15 in just a few seconds.

With reference now to both FIG. 1 and FIG. 2, pressurized sprayer 10 may be prepared for use by first pouring second substance 15 into second pressurized tank 14 as described above, then by attaching first pressurized tank 12 to a source of $CO_2$, not shown, thus filling first pressurized tank 12 with pressurized $CO_2$. More specifically, after second pressurized tank 14 is filled with second substance 15, shut-off valve 22 may be closed, thus isolating pressurized tanks 12 and 14 from dispensing head 20. Discharge line 18 may then be removed from dispensing head 20 and attached to the $CO_2$ source, which may be for example a cylinder containing $CO_2$ under pressure. Shut-off valve 22 may be opened to allow the $CO_2$ to flow through discharge line 18 and feed line 16, and flow into first pressurized tank 12. When first pressurized tank 12 is full, or has received the desired amount of propellant, shut-off valve 22 may again be closed, the $CO_2$ source may be disengaged from discharge line 18, and dispensing head 20 may be reattached. Pressurized sprayer 10 would then be ready for use.

First and second pressurized tanks 12 and 14 may include means for releasably attaching pressurized tanks 12 and 14 to feed line 16. Such releasably attachable means may include a threaded area for the receipt of matching threads on elbows 38 or 42, interlocking tabs on openable ends 28 and 32 and on elbows 38 and 42 that engage each other when oriented in a particular manner, and any other means for releasably attaching first and second pressurized tanks 12 and 14 to feed line 16. Elbows 38 and 42 and mixing tee 40 may be releasably attachable to each other or to feed line 16 or discharge line 18, as applicable, through similar means. First and second lengths of tubing 39 and 44 may be pressure resistant or pressure tolerant tubing, and may be made out of any one of a variety of materials, such as steel or aluminum, as will be readily apparent to one of ordinary skill in the art.

A method for using pressurized sprayer 10 may proceed as follows, with continued reference to both FIGS. 1 and 2. First, a desired amount of second substance 15, such as pepper spray, may be placed in second pressurized tank 14, by releasing elbow 42 and pouring second substance 15 through openable end 32. Second, elbow 42 may be replaced in openable end 32, and first pressurized tank 12 may then be filled with first substance 13 in the manner described above. The step of placing first substance 13 in first pressurized tank 12 pressurizes the invention and placed it in a position of readiness for use. Finally, when desired, trigger 24 may be actuated, thus causing first and second substances 13 and 15 to be dispensed from dispensing head 20 through nozzle 26 in the direction of, for example, a person or animal whose behavior is desired to be affected or altered.

In use, pressurized sprayer 10, when filled as described above, may force first and second substances 13 and 15 out through dispensing head 20 and nozzle 26. First substance 13, being under pressure, tends to move in the direction of lower pressure, according to a principle that is well known in the art. The ambient pressure outside pressurized sprayer 10 is lower than the pressure inside pressurized tanks 12 and 14, but until trigger 24 is actuated there is no pathway along which first substance 13 may travel to arrive at the area of lower pressure, and pressurized sprayer 10 thus remains in a quiescent state, with the pressure of first substance 13 tending to keep second substance 15 in second pressurized tank 14. This is especially true if, as in one embodiment of the invention, first pressurized tank 12 has a higher pressure than second pressurized tank 14. When trigger 24 is actuated, and a pathway created, first substance 13 tends to rush toward the lower pressure region outside pressurized sprayer 10 with such force that second substance 15 is carried along with it, potentially at great velocity.

As has been described, first and second pressurized tanks 12 and 14 are inverted with respect to each other. In one advantageous embodiment, second pressurized tank 14, containing second substance 15, which in this embodiment may be the chemical irritant, is adapted so that its openable end 32 points substantially in the direction of the ground, such that second substance 15 tends to collect at or near openable end 32. This configuration, most clearly suggested by FIG. 2, allows gravity to assist in the operation of pressurized sprayer 10 by ensuring that second substance 15 is positioned near elbow 42 and mixing tee 40, from which position second substance 15 may be readily gathered then propelled along discharge line 18 and out through nozzle 26 by first substance 13. If second pressurized tank 14 were oriented otherwise, first substance 13 may be less efficient in its propulsion of second substance 15.

The described configuration allows the present invention to be discharged at virtually any angle, meaning, for example, that a chemical spray may be directed around corners or may be delivered while running or negotiating obstacles. More specifically, the configuration of first and second pressurized tanks 12 and 14 allows first and second substances 13 and 15 to be discharged while first and second pressurized tanks are in virtually any position. There is no need to carefully position any component of pressurized sprayer 10 before actuating trigger 24 in order to ensure the proper discharge of first and second substances 13 and 15. The invention may further be adapted to be carried on a user's back, thus allowing access, for example, to a firearm carried at the side.

The foregoing description has described selected embodiments of a sprayer that includes two pressurized tanks physically and fluidly coupled to each other. One tank is inverted with respect to the other so that the top of one tank is adjacent to the bottom of the other tank, and vice versa. One tank contains a propellant such as carbon dioxide and the other contains a tear agent or other chemical irritant. The invention includes a shut-off valve adapted to regulate the flow of the chemical, and a dispensing head for accurate, controllable delivery.

While the invention has been particularly shown and described with reference to selected embodiments thereof, it will be readily understood by one of ordinary skill in the art that, as limited only by the appended claims, various changes in form and details may be made therein without departing from the spirit and scope of the invention.

I claim:

1. A pressurized sprayer comprising:

(1) a first pressurized tank having an openable end and a closed end, said first pressurized tank containing a first substance;

(2) a second pressurized tank having an openable end and a closed end, said openable end of said second pressurized tank maintained adjacent to said closed end of said first pressurized tank, said closed end of said second pressurized tank maintained adjacent to said openable end of said first pressurized tank, said second pressurized tank physically and fluidly coupled to said first pressurized tank, said second pressurized tank containing a second substance;

(3) a feed line fluidly coupling said first pressurized tank to said second pressurized tank, wherein said feed line comprises:

a first elbow coupled to said first openable end of said first pressurized tank;

a first length of pressure-tolerant tubing coupled to said first elbow;

a mixing tee coupled to said first length of pressure-tolerant tubing; and a second elbow coupled to said mixing tee and to said second openable end of said second pressurized tank;

(4) a shut-off valve adapted to regulate the flow of said first and second substances; and (5) a dispensing head coupled to said shut-off valve.

2. The invention of claim 1 further comprising a discharge line, said discharge line fluidly coupling said shut-off valve to said feed line.

3. The invention of claim 2 wherein said discharge line comprises:

(1) said mixing tee; and (2) a second length of pressure-tolerant tubing coupled to said mixing tee and to said shut-off valve.

4. The invention of claim 1 wherein said first substance is carbon dioxide.

5. The invention of claim 1 wherein said second substance is a chemical irritant.

6. The invention of claim 1 wherein said first and second pressurized tanks are high pressure tanks.

7. The invention of claim 1 wherein at least one of said first and second pressurized tanks includes means for releasably attaching said at least one pressurized tank to said feed line.

8. The invention of claim 1 wherein said second pressurized tank is smaller than said first pressurized tank.

* * * * *